United States Patent [19]

Liu et al.

[11] Patent Number: 5,472,692
[45] Date of Patent: Dec. 5, 1995

[54] PRO-UROKINASE MUTANTS

[75] Inventors: Jian-Ning Liu, Brighton; Victor Gurewich, Cambridge, both of Mass.

[73] Assignee: New England Deaconess Hospital Corporation, Boston, Mass.

[21] Appl. No.: 87,163

[22] Filed: Jul. 2, 1993

[51] Int. Cl.[6] ............................. C12N 9/72; C12N 9/48; A61K 38/49
[52] U.S. Cl. .................. 424/94.63; 435/212; 435/215
[58] Field of Search .................. 424/94.63; 435/172.3, 435/212, 215, 226; 536/23.2; 514/12

[56] References Cited

U.S. PATENT DOCUMENTS 5,108,901 4/1992 Anderson ............................. 435/226

OTHER PUBLICATIONS

Harris, T. J. R. "Second–Generation Plasminogen Activators," *Protein Engineering* 1(6):449–458 (1987).
Brooks et al., *J. Comp. Chem.*, 4:187–217 (1983).
Heckel et al., *J. Comp. Aided Mol. Des.*, 2:7–14 (1988).
Liu et al., *Biochemistry*, 31:6311–6317 (1992).
Nienaber et al., *Biochemistry*, 31:3852–3861 (1992).
Peterson et al., *Biochem.*, 29:3451–57 (1990).
Wang et al. *J. Mol. Biol.*, 185:595–624 (1985).

*Primary Examiner*—Robert A. Wax
*Assistant Examiner*—Dian C. Jacobson
*Attorney, Agent, or Firm*—Fish & Richardson

[57] ABSTRACT

The invention relates to thrombolytically active pro-urokinase (pro-UK) mutants comprising the amino acid sequence of native pro-UK, but including a mutation which causes the pro-UK mutants to induce less fibrinogenolysis and non-specific plasminogen activation than native pro-UK, to have at least a 10-fold lower intrinsic activity than native pro-UK, and to have substantially the same fibrin promotion and thrombolytic activity after plasmin activation compared to native pro-UK when administered to a patient.

9 Claims, 7 Drawing Sheets

SEQUENCE LISTING ( 1 ) GENERAL INFORMATION:

( i i i ) NUMBER OF SEQUENCES:1

( 2 ) INFORMATION FOR SEQ ID NO: 1:

( i ) SEQUENCE CHARACTERISTICS:
        ( A ) LENGTH: 411
        ( B ) TYPE:amino acid
        ( C ) STRANDEDNESS: Not Relevant
        ( D ) TOPOLOGY: Not Relevant     ( x i ) SEQUENCE DESCRIPTION: SEQ ID NO: 1:

```
Ser  Asn  Glu  Leu  His  Gln  Val  Pro  Ser  Asn  Cys  Asp  Cys  Leu  Asn  Gly
                    5                        10                       15
Gly  Thr  Cys  Val  Ser  Asn  Lys  Tyr  Phe  Ser  Asn  Ile  His  Trp  Cys  Asn
               20                       25                       30
Cys  Pro  Lys  Lys  Phe  Gly  Gly  Gln  His  Cys  Glu  Ile  Asp  Lys  Ser  Lys
          35                       40                       45
Thr  Cys  Tyr  Glu  Gly  Asn  Gly  His  Phe  Tyr  Arg  Gly  Lys  Ala  Ser  Thr
     50                       55                       60
Asp  Thr  Met  Gly  Arg  Pro  Cys  Leu  Pro  Trp  Asn  Ser  Ala  Thr  Val  Leu
65                       70                       75                       80
Gln  Gln  Thr  Tyr  His  Ala  His  Arg  Ser  Asp  Ala  Leu  Gln  Leu  Gly  Leu
               85                               90                       95
Gly  Lys  His  Asn  Tyr  Cys  Arg  Asn  Pro  Asp  Asn  Arg  Arg  Arg  Pro  Trp
               100                              105                      110
Cys  Tyr  Val  Gln  Val  Gly  Leu  Lys  Pro  Leu  Val  Gln  Glu  Cys  Met  Val
               115                      120                      125
```

| | | | | | | | | | | | | | | |
|---|---|---|---|---|---|---|---|---|---|---|---|---|---|---|
| His | Asp 130 | Cys | Ala | Asp | Gly | Lys 135 | Lys | Pro | Ser | Ser | Pro 140 | Pro | Glu | Glu | Leu |
| Lys 145 | Phe | Gln | Cys | Gly | Gln 150 | Lys | Thr | Leu | Arg | Pro 155 | Arg | Phe | Lys | Ile | Ile 160 |
| Gly | Gly | Glu | Phe | Thr 165 | Thr | Ile | Glu | Asn | Gln 170 | Pro | Trp | Phe | Ala | Ala 175 | Ile |
| Tyr | Arg | Arg | His 180 | Arg | Gly | Gly | Ser | Val 185 | Thr | Tyr | Val | Cys | Gly 190 | Gly | Ser |
| Leu | Ile | Ser 195 | Pro | Cys | Trp | Val | Ile 200 | Ser | Ala | Thr | His | Cys 205 | Phe | Ile | Asp |
| Tyr | Pro 210 | Lys | Lys | Glu | Asp | Tyr 215 | Ile | Val | Tyr | Leu | Gly 220 | Arg | Ser | Arg | Leu |
| Asn 225 | Ser | Asn | Thr | Gln | Gly 230 | Glu | Met | Lys | Phe | Glu 235 | Val | Glu | Asn | Leu | Ile 240 |
| Leu | His | Lys | Asp | Tyr 245 | Ser | Ala | Asp | Thr | Leu 250 | Ala | His | His | Asn | Asp 255 | Ile |
| Ala | Leu | Leu | Lys 260 | Ile | Arg | Ser | Lys | Glu 265 | Gly | Arg | Cys | Ala | Gln 270 | Pro | Ser |
| Arg | Thr | Ile 275 | Gln | Thr | Ile | Cys | Leu 280 | Pro | Ser | Met | Tyr | Asn 285 | Asp | Pro | Gln |
| Phe | Gly 290 | Thr | Ser | Cys | Glu | Ile 295 | Thr | Gly | Phe | Gly | Lys 300 | Glu | Asn | Ser | Thr |
| Asp 305 | Tyr | Leu | Tyr | Pro | Glu 310 | Gln | Leu | Lys | Met | Thr 315 | Val | Val | Lys | Leu | Ile 320 |
| Ser | His | Arg | Glu | Cys 325 | Gln | Gln | Pro | His | Tyr 330 | Tyr | Gly | Ser | Glu | Val 335 | Thr |
| Thr | Lys | Met | Leu 340 | Cys | Ala | Ala | Asp | Pro 345 | Gln | Trp | Lys | Thr | Asp 350 | Ser | Cys |
| Gln | Gly | Asp 355 | Ser | Gly | Gly | Pro | Leu 360 | Val | Cys | Ser | Leu | Gln 365 | Gly | Arg | Met |
| Thr | Leu 370 | Thr | Gly | Ile | Val | Ser 375 | Trp | Gly | Arg | Gly | Cys 380 | Ala | Leu | Lys | Asp |
| Lys 385 | Pro | Gly | Val | Tyr | Thr 390 | Arg | Val | Ser | His | Phe 395 | Leu | Pro | Trp | Ile | Arg 400 |
| Ser | His | Thr | Lys | Glu 405 | Glu | Asn | Gly | Leu | Ala 410 | Leu | | | | | |

PRO-UROKINASE MUTANTS

BACKGROUND OF THE INVENTION

The invention relates to new forms of pro-urokinase useful for thrombolytic therapy.

Pro-urokinase (pro-UK) is a single-chain form of a serine protease precursor, which is activated by plasmin to form two-chain urokinase (UK). Both pro-UK and UK activate, or convert, the zymogen plasminogen to the active enzyme plasmin, which degrades a series of plasma proteins included in fibrin clots. Consequently, both pro-UK and UK have been used for the treatment of thromboembolism.

There are certain undesirable side effects which can be caused by such treatment. Both pro-UK and UK can cause non-specific plasminogen activation, which leads to the degradation of fibrin, fibrinogen (fibrinogenolysis), and certain parts of platelets and blood vessel walls, and hemorrhagic diathesis. Pro-UK is more selective, i.e., specific, in its plasminogen activation at low doses than UK, because it activates only fibrin-bound plasminogen, whereas UK activates any plasminogen. However, pro-UK's specificity at low doses can be lost when it is administered at the high doses required for thrombolytic efficacy.

Pro-UK has certain properties which make it resemble both an "inactive" zymogen and an "active" enzyme. On one hand, pro-UK's zymogenic properties include its inert behavior in plasma, its failure to form sodium dodecyl sulfate-stable inhibitor complexes, and its relative resistance to inhibition by diisopropylfluoro-phosphate (DFP) or Glu-Gly-Arg chloromethylketone, which are potent chemical inhibitors of UK. Pro-UK also has a 200-fold lower plasminogen activating activity than UK.

On the other hand, pro-UK's enzymatic properties include its measurable intrinsic activity against both synthetic substrates and plasminogen, which is $10^{4.0-4.3}$-fold higher than other serine protease zymogens such as trypsinogen or chymotrypsin. Pro-UK also has a lower Michaelis constant (KM) than UK against plasminogen, and, in the presence of fibrin fragment $E_2$, pro-UK has been shown to be fully active against plasminogen without being activated to the UK form.

In spite of its potential use as a thrombolytic agent, when it is given in therapeutic doses, pro-UK's high intrinsic enzymatic activity initiates the undesirable non-specific systemic plasminogen activation noted above. As a result, thrombolytic therapy with pro-UK can still be associated with deleterious side effects.

SUMMARY OF THE INVENTION

The present invention is based on the discovery that mutant forms of pro-UK can be designed that exhibit an attenuation of the undesirable intrinsic, non-specific enzymatic activity of naturally occurring, native pro-UK, but are at least as effective as native pro-UK in their ability to be promoted (activated) by fibrin (fragment Y or $E_2$), convert plasminogen into plasmin, and remain thrombolytically active after conversion into two-chain UK. As a result, these pro-UK mutants cause lower non-specific plasminogen activation and bleeding complications than native pro-UK when administered to a patient.

These pro-UK mutants are superior thrombolytic agents compared to native pro-UK, because they are promoted by fibrin to the same extent as native pro-UK, and therefore have the same fibrinolytic efficiency, but have a far greater specificity for fibrin-bound plasminogen than native pro-UK, because they are truly inert in plasma. As a result of this inert behavior, these pro-UK mutants can be administered to a patient at higher, more efficacious, dosages than native pro-UK.

Accordingly, the invention features a thrombolytically active pro-UK mutant that has the amino acid sequence of native pro-UK, wherein the sequence includes a mutation which causes the pro-UK mutant to induce less fibrinogenolysis and non-specific plasminogen activation than native pro-UK when administered to a patient. The mutation is preferably a substitution of a new amino acid for a native amino acid normally in the amino acid sequence of native pro-UK, which causes the pro-UK mutant to have at least a 10-fold lower intrinsic activity than native pro-UK, and to have substantially the same fibrin promotion and thrombolytic activity after plasmin activation compared to native pro-UK when administered to a patient.

As used herein, the term "native" means a naturally occurring, or wild type, form of a protein, or an amino acid in a naturally occurring protein. A "new" amino acid is one that is not normally located at a given location within a native protein. As used herein, the term "mutation" includes the substitution of a single new amino acid for a native amino acid, or the substitution of two or more new amino acids for two or more native amino acids.

In particular, the mutation can be a substitution of a new amino acid for a native amino acid normally in the flexible loop (amino acids 297 to 313) of native pro-UK. For example, the new amino acid can be substituted for $Lys^{300}$, $Gly^{299}$, and/or $Glu^{301}$, e.g., with alanine or histidine. In addition, the new amino acid can be substituted for $Lys^{313}$, e.g., with alanine or histidine, or for $Tyr^{306}$, e.g., with glycine.

In addition, the mutation can be a substitution of a new amino acid for $Ala^{175}$ and a second new amino acid for $Tyr^{187}$ to form a zymogen triad in the pro-UK mutant. For example, the new amino acid can be serine, and the second new amino acid can be histidine. The invention also features combination mutations, such as the introduction of two mutations to form the zymogen triad, and further including a substitution of a third new amino acid for $Lys^{300}$, and a fourth new amino acid for $Glu^{301}$. Such a mutant would have, for example, serine as the new amino acid, histidine as the second new amino acid, alanine or histidine as the third new amino acid, and alanine as the fourth new amino acid.

The invention further features a DNA molecule, e.g., a recombinant DNA molecule, which encodes any of the pro-UK mutants described herein. Such mutants can include single, double, or multiple substitutions. The invention also includes a cell, e.g., a mammalian, bacterial, or yeast cell, transformed with such a DNA molecule. The invention also features a method of making the pro-UK mutants described herein by transforming a cell with a DNA molecule encoding a pro-UK mutant, culturing the cell to express the mutant, and isolating the mutant.

In addition, the invention features a method of treating thromboembolism in a patient comprising administering a thrombolytic amount of any of the pro-UK mutants described herein to the patient. As used herein, the term "thrombolytic amount" is that amount of a pro-UK mutant that will lyse fibrin clots in the patient without inducing systemic bleeding.

Other features and advantages of the invention will be apparent from the following detailed description, and from the claims.

DETAILED DESCRIPTION

The drawings will first be briefly described.

The file of this patent contains at least one drawing executed in color. Copies of this patent with color drawings will be provided by the Patent and Trademark Office upon request and payment of the necessary fee.

Development of Pro-UK Mutants

The three-dimensional ("3-D") structures of UK and pro-UK have not yet been determined. However, it is known that the B-chain of pro-UK/UK (which is the protease domain) is significantly homologous with trypsin and chymotrypsin, and their precursors trypsinogen and chymotrypsinogen, respectively, whose 3-D structures are well known from X-ray crystallography. Since these homologies are greater than 30%, the backbone alignment of pro-UK/UK with these molecules is within about 1.0 Å or less for the core residues. Therefore, the predicted structure of pro-UK/UK is reliable.

"Homology" for amino acid sequences refers to the similarity or percent identity between two or more amino acid sequences. The homology of two given proteins may be determined, for example, by using sequence analysis software (e.g., the Sequence Analysis Software Package of the Genetics Computer Group, University of Wisconsin, Madison, Wis.). Homology percentage values are assigned to exact matches as well as sequences with conservative amino acid substitutions, e.g., the replacement of one amino acid by another, similar, amino acid, resulting in little or no change in the properties and activity of the resulting protein.

Pro-UK mutants were designed based on the structural homology of pro-UK/UK with trypsin(ogen) and chymotrypsin(ogen), and the discovery that pro-UK's fibrin specificity is mediated by its selective promotion by fibrin fragment $E_2$, Liu & Gurewich, Biochemistry, 31:6311–6317 (1992), which induces a particular conformational change in Glu-plasminogen. To design the pro-UK mutants, applicants developed a computer model of the 3-D structure of the protease domain (the B-chain) of pro-UK/UK based on the spatial coordinates for the polypeptide backbone of chymotrypsinogen and chymotrypsin, respectively, supplemented with the structures of elastase and trypsin(ogen). Applicants also used two molecular modelling programs, CHARMM, a program for macromolecular energy minimization and dynamics calculations, which was developed by the Harvard University Chemistry Department, and is described in Brooks et al., J.Comp.Chem., 4:187–217 (1983), and QUANTA®, which was developed by Silicon Graphics, Inc. (San Francisco, Calif., USA), which are incorporated herein by reference.

Figure 1:
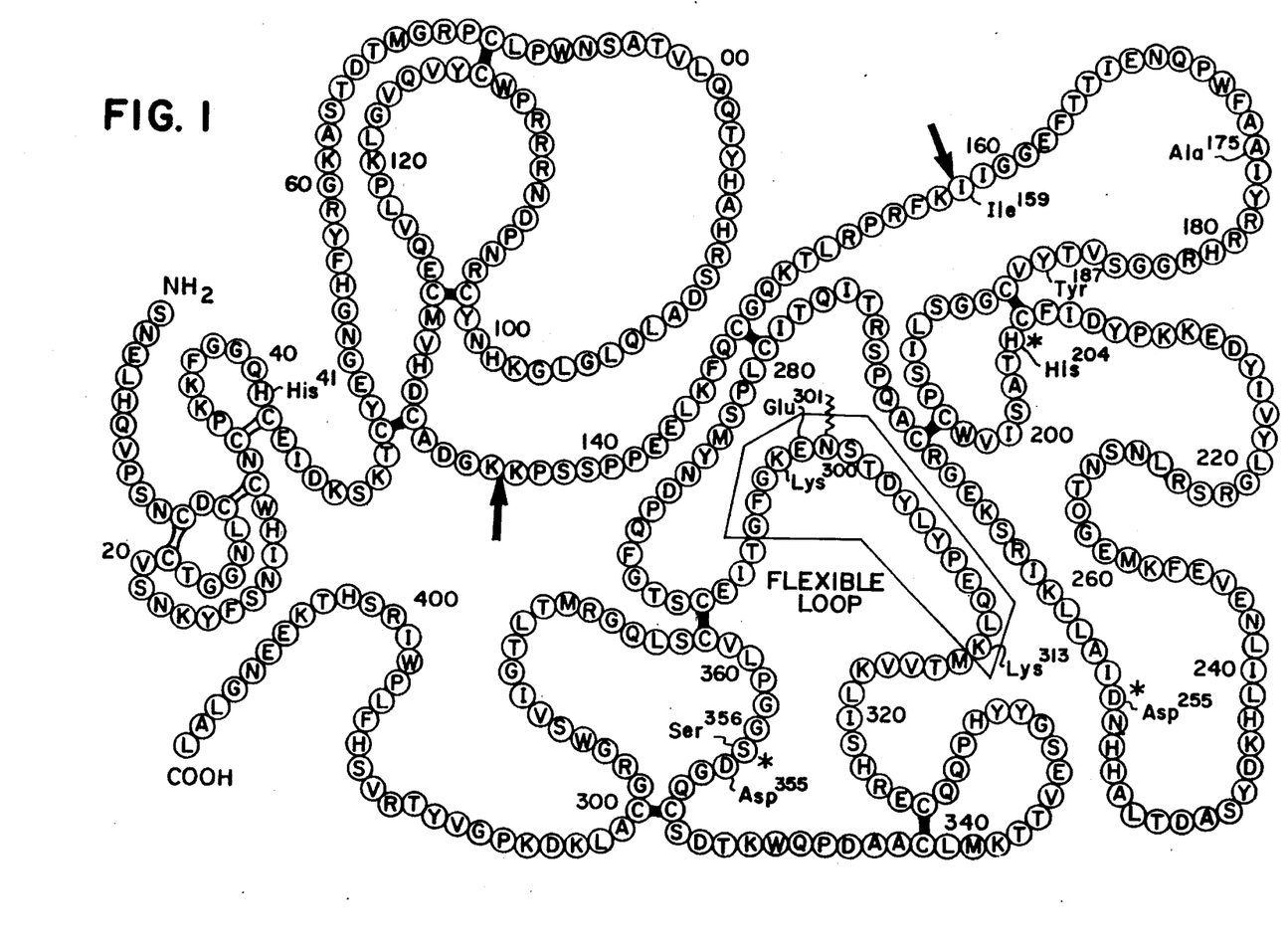
FIG. 1 is a schematic of the amino acid structure of pro-UK, showing the flexible loop and various specific amino acids.
Figure 2A:
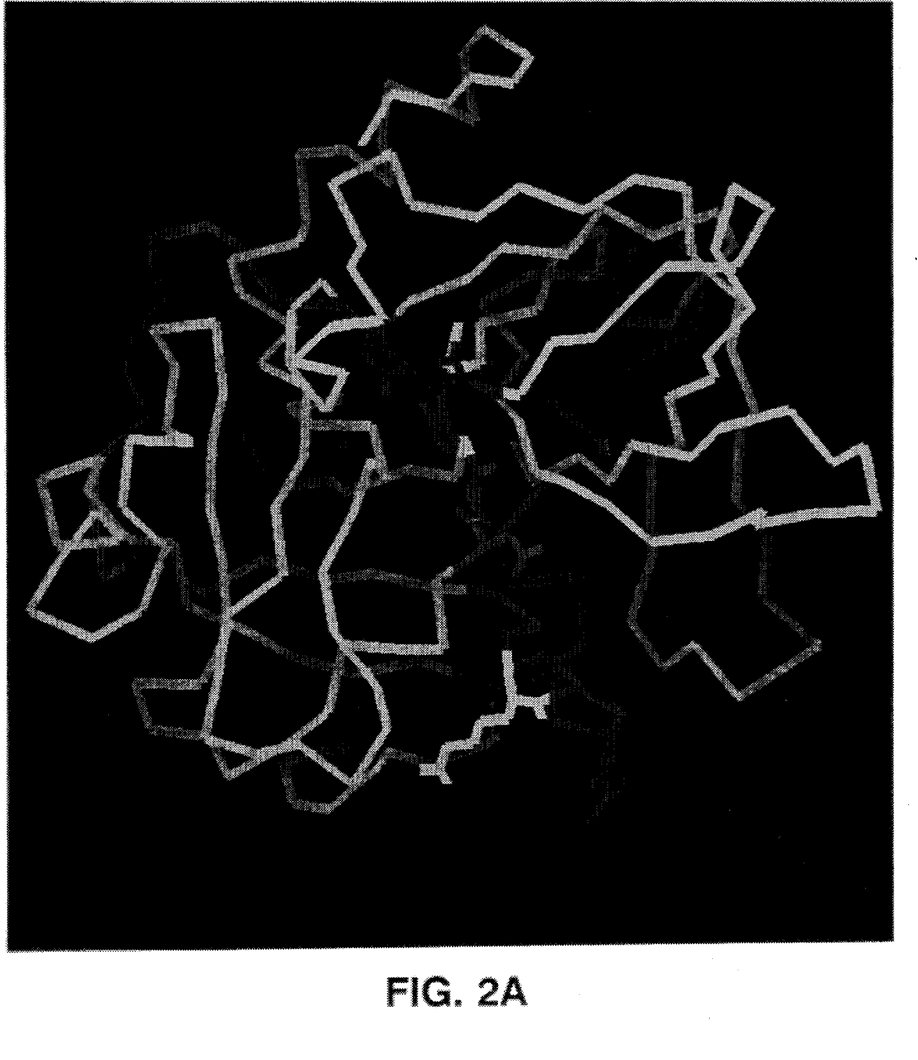
FIG. 2a is a computer-generated three-dimensional (3-D) model of pro-UK in the "inactive" conformation, which shows the active site (Ser$^{356}$, His$^{204}$, and Asp$^{255}$, in red) and the Lys$^{300}$ and Lys$^{313}$ (yellow) of the so-called "flexible loop" (in blue) not interacting with Asp$^{355}$ (green).
Figure 2B:
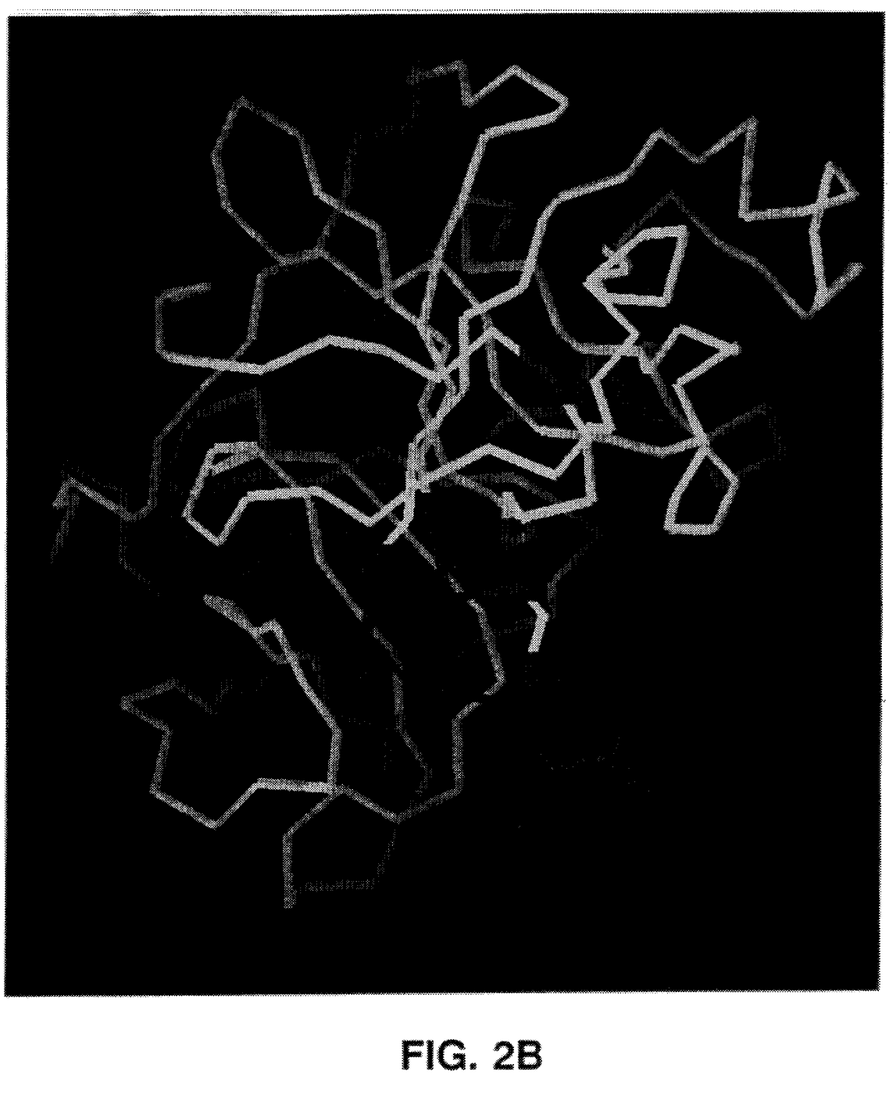
FIG. 2b is a computer-generated 3-D model of pro-UK in the "active" conformation, which shows the active site (Ser$^{356}$, His$^{204}$, and Asp$^{255}$, in red), and the Lys$^{300}$ and Lys$^{313}$ (yellow) of the so-called "flexible loop" (in blue) interacting with Asp$^{355}$ (green).

As shown in FIGS. 1, 2a, and 2b, this model clearly displays the three dimensional structure of the pro-UK B-chain (protease domain). The model is constructed by two sub-domains which are β-barrel structures similar to the structure of chymotrypsin(ogen), and has the following characteristics. The spatial coordinate of every atom in this B-chain is well defined. Ile$^{159}$, which is on the surface of the molecule, is covalently linked to the peptide 130–158 of the A chain. The "activation domain" of pro-UK, comprises three sequences (amino acid locations 297–313, 344–353, and 376–383). The sequence 297–313 forms the "flexible loop" (blue in FIGS. 2a and 2b) which is less flexible than a similar loop of chymotrypsinogen or trypsinogen, but is still "wobbly." When the flexible loop is in a certain conformation, the ε-positive charged amino group of the Lys$^{300}$ (yellow) in the loop interacts with the negatively charged carboxyl group of Asp$^{355}$ (green). This interaction pulls the active site Ser$^{356}$ almost into the ideal position in which the Ser$^{356}$ hydroxyl is in the most favorable position for interaction within the charge relay system which includes the other two major active site residues: a histidine and an aspartic acid (red in FIGS. 2a and 2b). The Lys$^{313}$ (yellow) also interacts with Asp$^{355}$ from another direction. Therefore, the active site and substrate binding pocket of pro-UK protease domain are predominately formed, for this moment, without conversion to the two-chain form. However, since the probability of this "active conformation" is only 0.5%, the uncleaved, single-chain pro-UK has only about 0.5% of the activity of the active two-chain form.

Figure 2C:
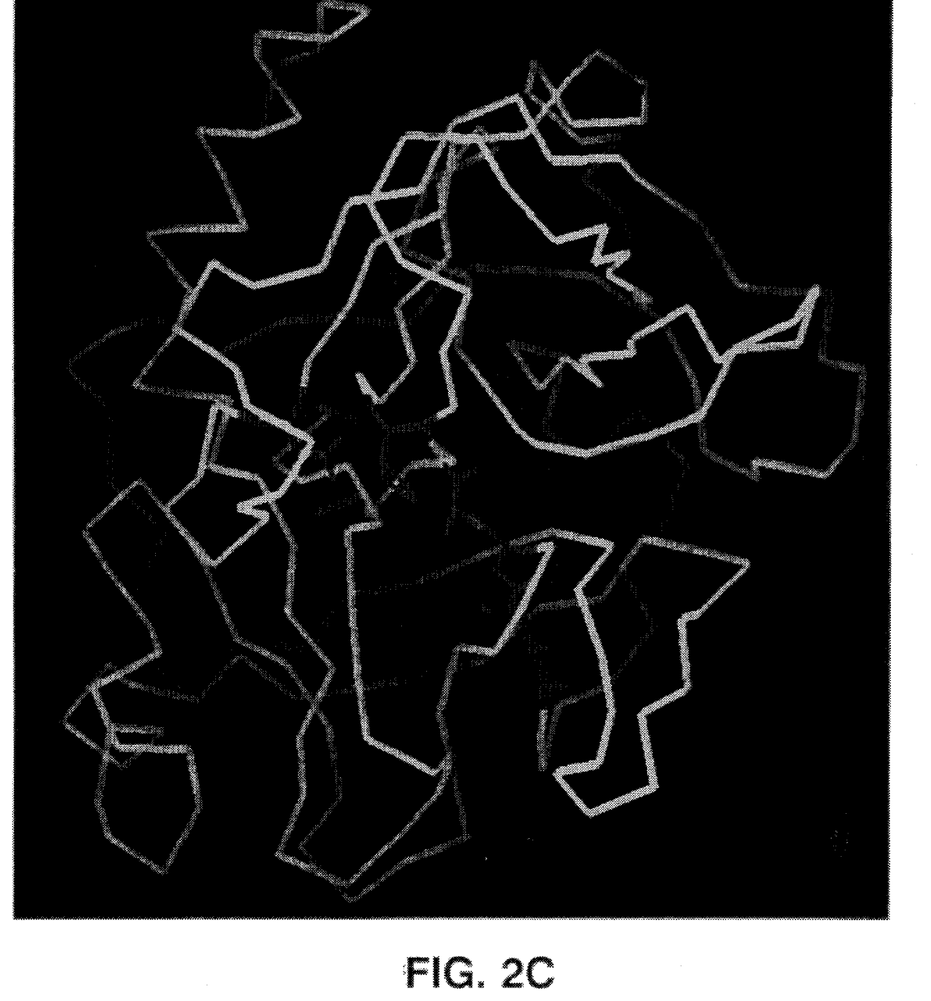
FIG. 2c is a computer-generated 3-D model of two-chain UK, which shows the active site (Ser$^{356}$, His$^{204}$, and Asp$^{255}$, in red), Asp$^{355}$ (green), and the cleaved neo-amino terminal residue Ile$^{159}$ (purple).
Figure 3:
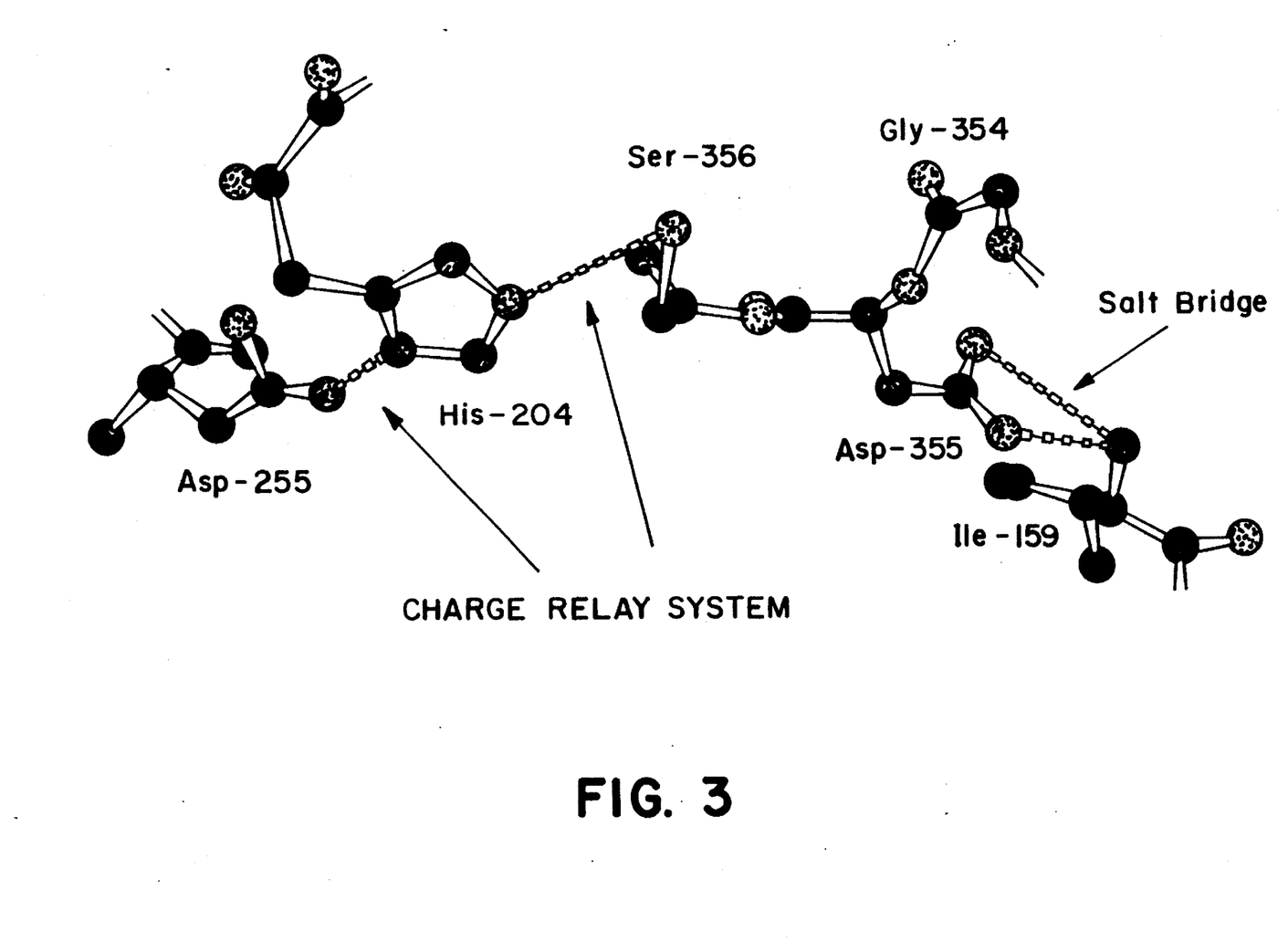
FIG. 3 is a schematic which shows the so-called "charge relay system" including Ser$^{356}$, His$^{204}$, and Asp$^{255}$, and a "salt bridge" between Asp$^{355}$ and Ile$^{159}$.

As shown in FIGS. 2c and 3, in the two-chain form, the neo-amino group of cleaved Ile$^{159}$ (purple in FIG. 2c) forms a stable "salt bridge" with Asp$^{355}$ (green in FIG. 2c), which stabilizes the activation domain and makes the molecule fully active. As an alternative, if an external force, such as an interaction from fragment $E_2$-bound plasminogen, stabilizes the active conformation of the "flexible" loop (yellow in FIG. 2c), the uncleaved single-chain form of pro-UK will also be fully active.

Additionally, the pro-UK model does not include the so-called "zymogen triad" of chymotrypsinogen (a hydrogen bond network formed by Asp$^{194}$, His$^{40}$, and Ser$^{32}$), because this triad is not present in the native pro-UK. His$^{40}$ and Ser$^{32}$ of the chymotrypsinogen triad are replaced in pro-UK by Tyr$^{187}$ and Ala$^{175}$, respectively. The "zymogen triad" is important for stabilizing the inactive conformation of a region of the active site (the oxyanion hole) of chymotrypsinogen.

Using this model, applicants selected and modelled specific amino acid substitutions in the protease domain of pro-UK and UK to design specific pro-UK mutants, and then constructed, expressed, and characterized certain of these mutants. Four classes of mutations which fulfill the desired objectives of decreased non-specific plasminogen activation and fully retained thrombolytic activity are described below.

Site-directed Mutations of Lys$^{300}$ of Pro-UK

Studies using X-ray crystallography have helped to explain why the single-chain zymogen form of most proteases has "no" activity, and how cleavage of a single bond induces formation of a fully active enzyme. Pro-UK, however, has more intrinsic activity than most other zymogens, but less than single-chain tissue plasminogen activator (SC-t-PA). In particular, trypsinogen and chymotrypsinogen have only about $10^{-6}$ of the activity of their respective activated two-chain enzyme forms. SC-t-PA has about $10^{-1.5}$ of the activity of two-chain t-PA. Pro-UK has about $10^{-2.3}$ of the activity of its two-chain derivative, UK.

A major aspect of the activation of a serine protease zymogen to the active enzyme is the movement of the neo-amino terminal α-amino group of the zymogen into a surface pocket of the zymogen where it can form a so-called "salt bridge" with an aspartic acid adjacent in the amino acid sequence to a serine in the active site of the protein. This sequence of events is shown schematically in FIG. 3. The salt bridge is an ionic bond or electrostatic interaction formed between the positively charged α-amino group of the neo-amino terminal of two-chain UK (Ile$^{159}$), or a surrogate in pro-UK, and the negatively charged carboxyl group of the side chain of the aspartic acid residue (Asp$^{355}$).

This salt bridge formation results in torquing of the serine hydroxyl into a new position most favorable for interaction within the charge relay, or proton transferring, system, which is the key of catalysis, and is formed by three major active site residues: His, Asp, and Ser (FIGS. 2a–2c (red), and 3). The salt bridge formation also stabilizes what has been called the "activation domain" of pro-UK comprising three sequences (297–313, 344–353, and 376–383).

In the inactive zymogens trypsinogen and chymotrypsinogen, these activation domains are not imaged in X-ray crystallograms, which has been attributed to their not being fixed in space, but rather being wobbly. These domains surround the substrate-binding pocket, which may explain the non-binding of zymogens to substrates. In the activated enzymes trypsin and chymotrypsin, these domains are fixed and are clearly visualized in X-ray crystallograms, as described in Huber et al., Acct.Chem.Res., 11:114–122 (1978).

In SC-t-PA, the ε-amino positive charge of Lys$^{416}$ (t-PA numbering) appears to provide a surrogate salt bridge effect through Asp$^{477}$ (t-PA numbering) to pull the active site Ser$^{478}$ (t-PA numbering) almost into the ideal position, as described in Heckel et al., J.Comp.AidedMol.Des., 2:7–14 (1988) and Peterson et al., Biochem., 29:3451–57 (1990). In pro-UK, there is a Lys$^{300}$ (pro-UK numbering) at the same position as the Lys$^{416}$ in SC-t-PA. The ε-amino positive charged group of the pro-UK Lys$^{300}$ is postulated to be a surrogate of the neo-terminal ε-amino group Ile$^{159}$ of UK. However, there is an adjacent Glu$^{301}$ which appears to attenuate its influence. There is also a glycosylation site at the Asn$^{302}$ residue, as well as a phosphorylation site at the nearby Ser$^{303}$ residue. This arrangement may explain the partial (relative to SC-t-PA) provision of a high (relative to chymotrypsinogen) intrinsic activity of pro-UK.

Based on these considerations, applicants have classified a group of mutants in which the residue Lys$^{300}$ and/or its surrounding residues are mutated to several different types of amino acid residues to adjust the electronic interaction between this position and Asp$^{355}$ (pro-UK numbering), which lowers the intrinsic activity as much as possible, but retains the fibrin promoting ability and two-chain form activity of native pro-UK. This group of mutants is illustrated by the following pro-UK mutants numbered 1 through 5. These mutants were created by the techniques of site-directed mutagenesis and gene expression which are described below.

Mutant 1: Lys$^{300}$→ Ala

The neutral amino acid alanine (Ala) was substituted for the Lys$^{300}$ in pro-UK, which does not affect the folding of the molecule, but which was designed to eliminate the salt bridge between position 300 and Asp$^{355}$ to reduce the intrinsic activity. Once designed on the computer model, this mutant was created and tested as described below. The results showed that this mutant had almost no measurable intrinsic activity, and, consequently, was extremely stable in plasma, inducing no fibrinogen degradation at a concentration of greater than 10 mg/ml incubated for over 24 hours. This stability is at least 10-fold greater than a concentration at which native pro-UK induced a 50% degradation of plasma fibrinogen in vitro. This mutant's two-chain form activity (after plasmin activation) was attenuated (33% that of UK), as was its promotion by fibrin fragment E$_2$ (40% that of pro-UK).

Mutant 2: Lys$^{300}$→ His

As a second alternative, histidine (His) was substituted for the Lys$^{300}$ in the pro-UK model. Histidine is capable of acquiring a hydrogen ion to become positively charged at a pH of less than 6.5, but is not as strong as the ε-amino charge in lysine. In the pro-UK model, the imidazole group of His$^{300}$ is packed inside the molecule at a lower energy state than outside, because the imidazole group is rather hydrophobic. This allows the imidazole group to have a positive charge since it faces towards Asp$^{355}$, which makes the local environment acidic. Therefore, a weak salt bridge exists between Asp$^{355}$ and His$^{300}$ to make the His$^{300}$ behave like a weak Lys$^{300}$. Since the electrostatic charge of His is dependent on the local environment, and the His$^{300}$ is located in the flexible loop region (297–313) as described below, the modulator (fragment E$_2$) still regulates the intrinsic activity of pro-UK. Based on the Lys$^{300}$→ Ala data and the characteristics of His compared to Lys, the intrinsic activity of Mutant 2 should also be 10-fold lower than that of native pro-UK, but more than that of Mutant 1. However, both two-chain form activity and fibrin promoting ability should be retained, and should be more than that of Mutant 1, but less than that of native pro-UK.

Mutant 3: Gly$^{299}$→ His/Lys$^{300}$→ Ala

In the pro-UK model, the oxygen of the carbonyl group Gly$^{299}$ in the main chain of pro-UK forms a hydrogen bond with Asp$^{355}$. Such a bond formation also exists in chymotrypsinogen and trypsinogen. When Gly$^{299}$ is replaced with His in the model, a strong salt bridge forms between His$^{299}$ and Asp$^{355}$, which is stronger than the bridge formed between His$^{300}$ and Asp$^{355}$, and therefore prevents this salt bridge from forming. Also, the local environment of His$^{299}$ is less affected by any conformational changes of the flexible loop of pro-UK than by changes of the active site, substrate binding pocket, or other inside areas. In contrast, the His$^{300}$ mutant (Mutant 2) should have the opposite behavior, i.e., it should be more regulated by conformational changes of the loop area. Based on the characteristics of His compared to Gly, the intrinsic activity and two-chain form activity of Mutant 3 should be 2-fold greater than those of Mutant 2. However, its fibrin promoting ability should be more than 20% lower than that of Mutant 2, but more than that of Mutant 1.

Mutant 4: $Lys^{300} \rightarrow Ala/Glu^{301} \rightarrow Ala$

When the positively charged $Lys^{300}$ is replaced by a neutral alanine, the negative charge of $Glu^{301}$ becomes too strong to attract the α-amino group of $Ile^{159}$ from its interaction with $Asp^{355}$. This results in a reduction of thrombolytic activity in the activated two-chain form (UK) of Mutant 1. Therefore, a double mutant was designed to solve this problem by replacing both $Lys^{300}$ and $Glu^{301}$ with neutral alanine. Based on the model, and characteristics of neutral Ala compared Lys and Glu, Mutant 4 should have characteristics almost identical those of Mutant 1, but should have a 2-fold higher two-chain form activity than Mutant 1.

Mutant 5: $Lys^{300} \rightarrow His/Glu^{301} \rightarrow Ala$

This mutant is a combination of Mutants 2 and 4. Based on the characteristics of the $Ala^{300}$ pro-UK Mutant 1, the positively charged residue (300) is important to promote both the single-chain intrinsic activity, and the two-chain form activity. Therefore, this double mutant, Mutant 5, should be similar to Mutant 2 in the intrinsic activity and the fibrin promoting ability, but should have a higher two-chain form activity.

Mutants 1 to 5 show how the intrinsic activity, two-chain form activity, and fibrin promoting ability can be adjusted compared to native pro-UK. These adjustments are accomplished in actual pro-UK mutants by the combined techniques of site-directed mutagenesis and structure modelling. These mutants essentially achieve the three objectives of (1) reduced fibrinogen degradation (low intrinsic activity), (2) unaltered fibrin promotion (retained fibrin promoting ability), and (3) equal activity after plasmin activation compared to native pro-UK (two-chain form activity). Therefore, these mutants will have a high therapeutic utility.

Site-directed Mutations of the Flexible Loop of Pro-UK

Another structure of pro-UK which is critical to the intrinsic activity, is the so-called "flexible loop" formed by amino acids 297–313 (FIG. 1, FIGS. 2a and 2b (blue)), which is the most disordered, or wobbly, area in all serine proteases and their zymogens. This region may provide a mechanism for certain modulations of enzyme/zymogen function.

This loop is cleaved in chymotrypsin, but in t-PA and pro-UK, a $Lys^{416/300}$ mutant is involved in the intrinsic activities. Based on the pro-UK/UK model, a distinct "active" conformation of this loop was identified (blue in FIG. 2b), which, in native pro-UK, is in a dynamic equilibrium with other various "inactive" conformations. In the "active" conformation, the only positively charged residue of the loop, $Lys^{300}$, is positioned to face the inside of the molecule to form a salt bridge with $Asp^{355}$ (green), resulting in a fully active catalytic site. By contrast, in the "inactive" conformations, the loop (blue in FIG. 2a) is flipped to place the $Lys^{300}$ positive charge facing out of alignment with $Asp^{355}$ (green), which makes the zymogen inactive.

The observed activity of pro-UK indicates that the equilibrium favors the inactive conformations, with only 0.5% in the active conformation, which corresponds to the percent of intrinsic activity of pro-UK relative to its active, two-chain form (UK).

Initial studies showed that in the flexible loop, the side chains of three negatively charged residues ($Glu^{301}$, $Asp^{305}$, and $Glu^{310}$) are always located on the side of the loop opposite from $Lys^{300}$. When the side chains of the negatively charged residues are held outside of the molecule, the ε-amino group of $Lys^{300}$ will have a high probability to form a salt bridge with $Asp^{355}$. In other words, the active conformation is favored when three negatively charged residues are held outside of the molecule.

When pro-UK interacts with fragment $E_2$-bound Glu-plasminogen, external electrostatic forces from the fragment $E_2$-Glu-plasminogen complex stabilize the active conformation by attracting these three negatively charged side chains ($Glu^{301}$, $Asp^{305}$ & $Glu^{310}$) out of the molecule. Therefore, $Lys^{300}$ is positioned to face the inside of the molecule and forms a salt bridge with $Asp^{355}$. As a result, pro-UK becomes fully active without converting to the two-chain form.

A site-directed mutation of the flexible loop which can further increase the flexibility of the loop, will lower the probability of the "active" conformation to less than 0.5%. If this mutant retains a similar two-chain form activity after conversion to two chain form, and retains a similar fibrin promoting ability compared to native pro-UK, it will be a superior activator which achieves the three proposed objectives. Such a mutant would have a lower intrinsic activity in plasma, but would be fully active in the presence of fibrin (fragment $E_2$) and in the two-chain form.

Based on these considerations, applicants have classified a second group of mutants which reduce the probability of the "active" conformation, but retain the inducibility of the "active" conformation by the fragment $E_2$-Glu-plasminogen complex, as well as two-chain form activity. This group of mutants is illustrated by the following pro-UK mutant numbered 6.

Mutant 6: $Tyr^{306} \rightarrow Gly$

Based on the concept that the intrinsic activity of pro-UK is a function of the equilibrium between the "active" and "inactive" conformations, an increase in the loop flexibility should decrease the intrinsic activity. Therefore, a $Tyr^{306} \rightarrow Gly$ mutant was designed in which the β-turn structure of the loop is broken to increase its flexibility. As a result, this mutant should have a reduced intrinsic activity, but the fragment $E_2$ promotion, the two-chain activity, and plasmin activation should be preserved. Therefore, Mutant 6 would have a good therapeutic utility.

Site-directed Mutations of $Lys^{313}$ of Pro-UK $Lys^{313}$ of pro-UK is another surrogate of the neo-terminal α-amino group of UK. As shown in FIGS. 1 and 2b, $Lys^{313}$ (yellow) can behave like $Lys^{300}$ to form a salt bridge with $Asp^{355}$ (green) which also should result in an increase of intrinsic activity of the pro-UK. The interaction of $Lys^{313}$ with $Asp^{355}$ is regulated by the movement of the flexible loop. Therefore, the elimination of this interaction will further reduce the intrinsic activity of pro-UK. Based on these considerations, applicants have designed the following Mutants 7 and 8.

Mutant 7: Lys$^{313}$→ Ala

As shown in FIGS. 1 and 2b, Lys$^{313}$ (yellow in FIG. 2b) is located on the end of flexible loop (297–313 in FIG. 1, blue in FIG. 2b) and close to Asp$^{355}$ (green). Similar to Lys$^{300}$, its e-amino positive charge acts as a surrogate of the neo-terminal α-amino group in UK to form a salt bridge with Asp$^{355}$ from a direction opposite to that of Lys$^{300}$. Advantageously, this mutant does not affect the activity of two-chain UK, since the salt bridge is broken when the neo-terminal amino group (Ile$^{159}$) has been generated to competitively form another salt bridge with Asp$^{355}$ in the two-chain UK.

By contrast, Lys$^{300}$ does affect two-chain form activity, since the charge interaction between Lys$^{300}$ and Asp$^{355}$ exists in the two-chain form and contributes to the two-chain form activity. Similarly, there is also a Lys residue in the comparable amino acid position of SC-t-PA which has been demonstrated to be involved in its high intrinsic activity.

Mutant 8: Lys$^{313}$→ His

In this mutant, His, which has a positive charge lower than that of Lys, is used to replace Lys$^{313}$. This mutant is designed as an adjustment of Mutant 7, based on a rationale similar to that described with respect to Mutant 2 above.

Both Mutants 7 and 8 should have a lower intrinsic activity than that of native pro-UK, because they prevent the formation of the salt bridge with the Lys$^{313}$, but higher than that of Mutants 1 or 2. Their two-chain form activities should be essentially the same as that of native UK (two-chain form). Their fibrin promoting ability also should be retained, and be close to that of native pro-UK. Therefore, these mutants also would be clinically useful.

Site-directed Mutations to Form a "Zymogen Triad" in Pro-UK

X-ray structures of chymotrypsin and chymotrypsinogen show that the formation of a hydrogen bond network by a "zymogen triad" (consisting of Asp$^{194}$, His$^{40}$ and Ser$^{32}$, chymotrypsin numbering) is important to stabilize an inactive conformation of a region of the active site (the oxyanion hole) of chymotrypsinogen. However, applicants found that this zymogen triad does not occur in either pro-UK or t-PA. His$^{40}$ and Ser$^{32}$ of the chymotrypsinogen triad are represented by Tyr$^{187}$ and Ala$^{175}$ in pro-UK, respectively. This missing triad may also contribute to higher intrinsic activity of pro-UK or t-PA.

As a alternative approach to designing a pro-UK mutant with the desired characteristics, a "zymogen triad" can be created in native pro-UK to reduce its intrinsic activity without affecting the other functions necessary for fibrinolytic activity.

Mutant 9: Ala$^{175}$→ Ser/Tyr$^{187}$→ His

This double mutant was designed to introduce a "zymogen triad" similar to that found in chymotrypsinogen into pro-UK. This mutation should reduce the intrinsic activity of pro-UK, but not affect the promotion by fragment E$_2$, and the activity of the two-chain form. Therefore, this mutant should also achieve the three objectives stated above, and be useful as a thrombolytic agent.

Combination Mutations

Applicants have discovered that the intrinsic activity of pro-UK depends on several different intra-molecular interactions which include 1) Lys$^{300}$ or Lys$^{313}$ as a surrogate of the neo-terminal α-amino group of UK in the single-chain form; 2) the lack of a "zymogen triad"; and 3) the lower flexibility and the higher probability of the active conformation of the flexible loop (297–313). Consequently, a mutation based on just one aspect, would not maximally eliminate the intrinsic activity, which is damaging, without diminishing the two-chain form activity and fibrin promoting activity, which are required for thrombolytic activity. However, a multi-mutation affecting two or more of these molecular interactions can achieve an optimal pro-UK mutant. Based on these considerations, applicants have designed a group of combination mutants which is illustrated by the following Mutants 10 through 17.

All of Mutants 10 through 17 have an artificial zymogen triad, which decreases intrinsic activity, and most have the Lys$^{313}$ neutralized or made less positive to prevent the formation of, or weaken, the salt bridge formation, which also decreases the intrinsic activity. Similarly, several of these combination mutants have the Lys$^{300}$ neutralized or made less positive. Tyr$^{306}$→ Gly mutations reduce the probability of the active conformation of the flexible loop by providing more flexibility, and Glu$^{301}$→ Ala mutations interrupt the interaction between Ile$^{159}$ and Asp$^{355}$, and hence retain the two-chain form activity.

Mutant 10: Ala$^{175}$→ Ser/Tyr$^{187}$→ His/Lys$^{313}$→ Ala

Mutant 11: Ala$^{175}$→ Ser/Tyr$^{187}$→ His/Tyr$^{306}$→ Gly

Mutant 12: Ala$^{175}$→.Ser/Tyr$^{187}$→ His/Lys$^{313}$→ His

Mutant 13: Ala$^{175}$→ Ser/Tyr$^{187}$→ His/Tyr$^{306}$→ Gly/ Lys$^{313}$→ Ala

Mutant 14: Ala$^{175}$→ Ser/Tyr$^{187}$→ His/Lys$^{300}$→ Ala/ Glu$^{301}$→ Ala/Lys$^{313}$→ Ala Mutant 15: Ala$^{175}$→ Ser/Tyr$^{187}$→ His/Lys$^{300}$→ His/ Glu$^{301}$→ Ala/Lys$^{313}$→ Ala Mutant 16: Ala$^{175}$→ Ser/Tyr$^{187}$→ His/Lys$^{300}$→ Ala/ Glu$^{301}$→ Ala/Lys$^{313}$→ His Mutant 17: Ala$^{175}$→ Ser/Tyr$^{187}$→ His/Lys$^{300}$→ His/ Glu$^{301}$→ Ala/Lys$^{313}$→ His All of these mutants should optimally accomplish the three proposed objectives of: (1) low intrinsic activity and high stability in plasma, (2) unaltered fibrin promoting ability and remarkably high fibrin-specificity, and (3) equal two-chain form activity after plasmin activation compared to native pro-UK. Therefore, these mutants should efficiently dissolve thrombotic clots at a higher dose than native pro-UK without inducing bleeding complications. Moreover, they should be useful as medications to prevent the formation of occlusive fibrin thrombi, because they are very inert in plasma without fibrin, and hence should be extremely safe. Consequently, these mutants have a high therapeutic utility.

Production of Pro-UK Mutants
Oligonucleotide-Directed Mutagenesis

One type of site-directed mutagenesis that is suitable to produce the pro-UK mutants described herein is oligonucleotide-directed mutagenesis, which allows the specific alteration of an existing DNA sequence, e.g., native pro-UK. The gene encoding native pro-UK is well-characterized and is available, e.g., from Dr. David Dichek (NIH) and Dr. Paolo Sarmientos (Primm, Milano, Italy). The ATCC No. is DNA 57329 or Bact/phage 57328. The sequence is also available from the NIH computer database Protein Identity Resource under the name UKHU. The amino acid sequence of pro-UK is shown in FIG. 1 (SEQ ID No: 1).

Oligonucleotide-directed mutagenesis is accomplished by synthesizing an oligonucleotide primer whose sequence contains the mutation of interest, hybridizing the primer to a template containing the native sequence, and extending it with T4 DNA polymerase. The resulting product is a heteroduplex molecule containing a mismatch due to the mutation in the oligonucleotide. The mutation is "fixed" upon repair of the mismatch in, e.g., E. coli cells. The details of this method are described, e.g., in Ausubel et al. (eds.), CurrentProtocolsinMolecularBiology, Chapter 8.1 (Greene Publishing Associates 1989, Supp. 13), which is incorporated herein by reference.

Figure 4:
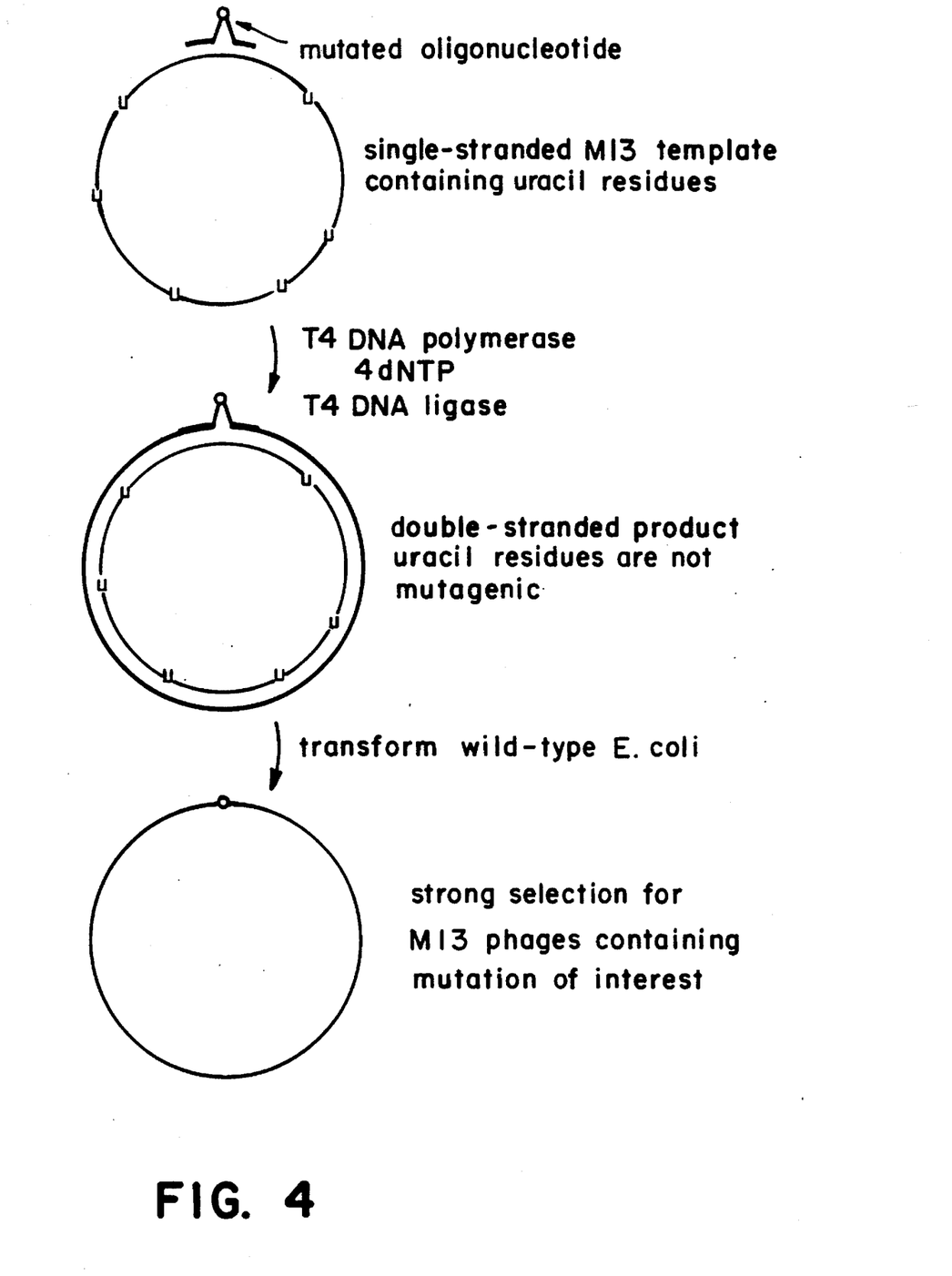
FIG. 4 is a schematic representation of a form of oligonucleotide-directed mutagenesis suitable to create the pro-UK mutants of the invention.

The basis of this site-directed mutagenesis method is the use of a DNA template containing a small number of uracil residues in place of thymine (FIG. 4). The uracil-containing DNA is produced in an E. coli dut⁻ ung⁻ strain. In this combined dut⁻ ung⁻ mutant, deoxyuridine is incorporated into DNA in place of thymidine and is not removed. Thus, vectors containing the sequence to be changed can be grown in a dut⁻ ung⁻ host to prepare uracil-containing DNA templates for site-directed mutagenesis. As shown in FIG. 4, the mutated oligonucleotide primer is annealed to the DNA template and treated with T4 DNA polymerase and T4 DNA ligase to produce a double-stranded circular molecule.

The oligonucleotide primer should be of high quality; i.e., purified from lower molecular weight contaminants that arise from incomplete DNA synthesis. In some cases, especially for oligonucleotides larger than 40 nucleotides, purification by polyacrylamide gel electrophoresis may be necessary.

For the in vitro reactions typical of site-directed mutagenesis protocols, uracil-containing DNA templates are indistinguishable from normal templates. Since dUMP in the template has the same coding potential as TMP, the uracil is not mutagenic. Furthermore, the presence of uracil in the template is not inhibitory to in vitro DNA synthesis. Thus, this DNA can be used as a template for the production of a complementary strand that contains the desired DNA sequence alteration, but contains only TMP and no dUMP residues.

After completing the in vitro reactions, uracil is removed from the template strand by the action of uracil N-glycosylase, e.g., or by introducing the unfractionated products of the in vitro reaction into wild-type (dut⁺ ung⁺) E. coli cells. Treatment with the glycosylase releases uracil, producing lethal apyrimidinic (AP) sites in the template strand. Thus, the template strand is rendered biologically inactive and the majority of progeny arise from the infective complementary strand which contains the desired alteration. This results in highly efficient mutant DNA production (typically 50%), and allows mutant DNAs to be screened by DNA sequence analysis.

Several variations of in vitro mutagenesis by primer extension that yield mutants with high efficiency have been developed, as described in Smith, Ann.Rev.Genet., 19:423–463 (1986). The procedure described here is a simple site-directed mutagenesis protocol applied to a special uracil-containing template which allows rapid and efficient recovery of mutant DNAs as originally described in Kunkel, Proc.Natl.Acad.Sci.U.S.A., 82:488–492 (1985), and Kunkel et al., Meth.Enzymol., 154:367–382 (1987), which are all incorporated herein by reference. In principle, this same template can be applied to most of the other protocols.

Mutant 1 was created by ligating the pro-UK gene into the HindIII/XbaI cite of plasmid M13mp18, transforming this plasmid into E. coli, isolating ssDNA, and performing oligonucleotide-directed mutagenesis as described above.

Expression of Pro-UK Mutant DNA

Once the pro-UK DNA with the desired mutation is obtained, it must be cloned into a suitable expression vector. This vector must then be introduced into a cell line, e.g., bacterial, mammalian, or yeast, to express the pro-UK mutant, which is harvested from the culture medium, or from the yeast cells, and then purified. These techniques are well known to those of ordinary skill in the field of molecular biology and are described in detail, e.g., in Ausubel et al. (eds.), CurrentProtocolsinMolecularBiology, Chapters 9 and 16, supra; and Sambrook, Fritsch, and Maniatis, MolecularCloning (2d ed.), Chapter 16 (Cold Spring Harbor Laboratory Press, 1989), which are incorporated herein by reference.

There are several ways in which the mutant pro-UK gene can be introduced into a mammalian cell line. One method involves the transfection of a vector into Chinese hamster ovary ("CHO") cells. In this procedure, the mutant pro-UK gene is co-transfected with a selectable marker, becomes stably integrated into host cell chromosomes, and is subsequently amplified. The CHO cell system is preferred because it allows the production of large amounts of mutant pro-UK for long periods of time. Cell lines such as the CHO DXB11 or CHO DG44 are available from Lawrence Chasin, Columbia University. Cell line CHO GRA is available from Randall Koufman, Genetics Institute.

Another expression method involves the transfection of the vector including the mutant DNA into a PET-19B E. coli expression system (Novagen, Madison, Wis.). For example, after site-directed mutagenesis, the DNA encoding Mutant 1 ($Lys^{300} \rightarrow Ala$) was sequenced to ensure that the mutation had occurred, and was then ligated into the NdeI/XhaI cite of PET-19B, a highly efficient E. coli gene expressing system (Novagen, Madison, Wis.), and transformed into E. coli. The transformed E. coli were cultured and induced to express the pro-UK mutant by addition of the inducer IPTG at log phase.

Once a vector has been introduced into a mammalian cell line, it is also desirable to increase expression of the desired protein, e.g., the mutant pro-UK, by selecting for increased copy numbers of the transfected DNA within the host chromosome. Co-amplifying transfected DNA results in a 100- to 1000-fold increase in the expression in the protein encoded by the transfected DNA. There are more than 20 selectable and amplifiable genes that have been described in the literature, but the most experience and success has been with methotrexate selection and amplification of transfected dihydrofolate reductase genes. For example, dihydrofolate reductase-deficient CHO cells may be used to obtain high level of expression of mutant pro-UK genes through co-amplification by selection for methotrexate resistance.

Amplification Using CHO Cell Expression Vectors

Figure 5:
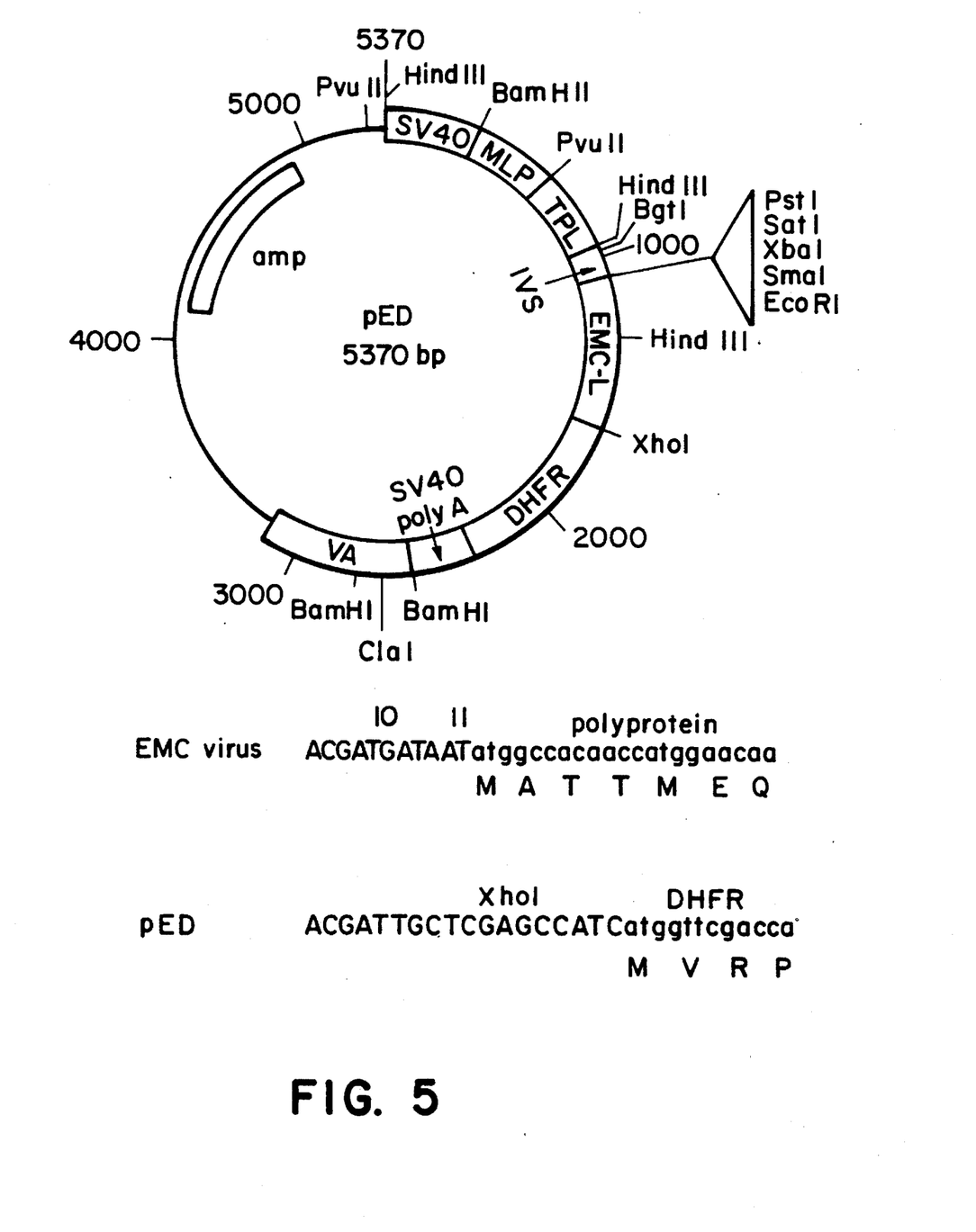
FIG. 5 is a schematic map of the dicistronic mRNA expression vector pED, which is suitable for expression of the pro-UK mutants in mammalian cells.

The pED series of dicistronic vectors can be used to obtain high-level expression of a targeted gene in stably transfected cells (FIG. 5). These vectors carry a cloning sequence for insertion of a target gene, e.g., the mutant pro-UK gene, followed by the selectable and amplifiable marker gene, dihydrofolate reductase ("DHFR"). DHFR-deficient CHO cells transformed with the appropriate vector are selected by their ability to grow in nucleoside-free medium. Subsequent selective cycling in the presence of increasing concentrations of methotrexate, which is a potent inhibitor of DHFR function, results in amplification of the integrated DNA and increased expression of the desired gene product. The pED vectors shown in FIG. 5 are described in Kaufman, et al., Nucl.Acids.Res., 19:4485–4490 (1991), which is incorporated herein by reference.

The CHO cells may be transfected with the mutant pro-UK and DHFR genes in a suitable vector, e.g., pED, using either electroporation, calcium phosphate, or liposome-mediated techniques, which are described in detail in CurrentProtocolsinMolecularBiology. The calcium phosphate treatment followed by glycerol shock is preferred for the CHO DXB11 cells. The transfected cells are then placed in selective medium, and after several days of growth, large healthy colonies with approximately 500 cells are be picked for amplification. The selected colonies are grown on separate plates prior to amplification.

Before amplifying the stable transfectants, cellular DNA should be analyzed by Southern analysis, or RNA should be analyzed by using a functional assay for the mutant pro-UK, to insure that the cells have integrated the desired mutant pro-UK gene. The selected cells are then placed into a methotrexate solution, which increases the level of selection, because methotrexate is a potent inhibitor of DHFR. By splitting the cells into this medium, one is selecting for cells making elevated levels of DHFR. This is generally accomplished by increasing the copy number of the transfected DHFR gene. At the same time, the mutant pro-UK gene, which was co-transfected with the DHFR gene, is also increased in copy number. Higher and higher levels of methotrexate are used to select out the cells that have the highest copy number of the DHFR gene, and hence, desired mutant pro-UK gene. When the cells grow in 20 to 80 μM methotrexate, the cells should contain 500 to 2000 copies of the transfected mutant pro-UK gene.

Extracting and Purifying Pro-UK Mutants

After the mutant pro-UK is expressed, e.g., by a mammalian or bacterial cell line, it must be extracted from the culture medium and purified. In the case of yeast cell culture, the yeast cells must first be disrupted, e.g., by mechanical disruption with glass beads to produce a cell extract that contains the mutant pro-UK. Purification of active mutant pro-UK from culture medium or cell extracts generally involves the steps of 1) liquid/liquid phase extraction or an initial filtration step, 2) hydrophobic affinity chromatography, 3) antibody affinity chromatography, and 4) gel filtration chromatography. These steps are well known to those of ordinary skill in the field of molecular biology, and are described in detail in CurrentProtocolsinMolecularBiology, Chapter 10.

The E. coli cells containing pro-UK Mutant 1 were lysed by sonication, and the lysate was applied to a nickel affinity chromatography column since poly-His is inserted ahead of the N-terminal of pro-UK with an enterokinase cleavage site (DDDDK). The purified pro-UK mutant was incubated with immobilized enterokinase to remove the N-terminal poly-His with a re-chromatography on a nickel affinity column. The sample was further purified by chromatographies through S-Sepharose, hydroxyapatite, Sephacryl S-200, and benzamidine columns after refolding as described in Winkler & Blaber, Biochemistry, 25:4041–4045 (1986), and Orsini et al, Eur.J.Biochem., 195:691–697 (1991). Any small amount of contaminating UK was removed by treatment with diisopropyl fluorophosphate (DFP).

Analysis of Pro-UK Mutants

The properties of the pro-UK mutants can be compared with rec-pro-UK produced by E. coli, as was done for Mutant 1. The intrinsic activity, fragment $E_2$ promotion of Glu-plasminogen activation at early time points, and the sensitivity to plasmin activation and clot lysis in a plasma milieu are tested to determine an assay profile which can be obtained with small amounts of the pro-UK mutants and which predicts how the mutant will perform as a thrombolytic agent in vivo.

Intrinsic Activity Assays

These assays are based on a kinetic analysis of the hydrolysis of S2444, a synthetic substrate for UK, and the activation of Glu-plasminogen.

S2444hydrolysis: 4.0 nM of UK or 1.0 μM of a pro-UK Mutant 1 was incubated with a range of concentrations (0.03, 0.06, 0.12, 0.18, 0.24, 0.3, 0.6, 1.2, 1.8 and 2.4 mM) of S2444 in 0.05 M sodium phosphate, 0.15 M NaCl, 0.2% BSA and 0.01% Tween 80 (pH 7.8) at room temperature. The reaction rate was measured by the linear OD increase with time at 410 nm against a reference wavelength of 490 nm (410/490 nm) on a microtiter plate reader. Mutant 1 showed almost no S2444 hydrolysis activity.

Glu-plasminogenactivation: Time-absorbance curves of Glu-plasminogen activation were obtained by measuring the OD increase of a reaction mixture with time at the selected wave length 410 nm and reference wave length 490 nm (410/490 nm) on a microtiter plate reader (Dynatech MR 5000). The reaction mixture contained S2251 (1.5 mM), Glu-plasminogen (1.0, 1.5, 2.5, 3.5, 4.5, 5.5, 7.5 and 10.0 μM) and UK (0.2 nM) or pro-UK Mutant 1 (5.0 nM). The reactants were made up in 0.05 M sodium phosphate, 0.15 M NaCl, 0.2% BSA, 0.01% Tween-80, pH 7.8 and incubated at room temperature. Mutant 1 showed a plasminogen activation activity of about 4 IU/mg, which is only one percent of that of native pro-UK, which has an activity of about 400 IU/mg.

Assay for Plasminogen Activation by Fibrin Fragment E-2

Glu-plasminogen activation by pro-UK Mutant 1 in the presence of fragment E-2 was determined by measuring the OD increase with time in a reaction mixture at 410 nm against a reference wavelength of 490 nm (410/490 nm) on the microtiter plate reader. The reaction mixture contained 1.5 mM S2251, a synthetic substrate for plasmin, Glu-plasminogen (1.0, 2.0, 4.0 & 8.0 μM), 5.0 μM of fragment E-2, and 1.0 nM of pro-UK Mutant 1 in 0.05 M sodium phosphate, 0.15 M NaCl, 0.2% BSA, 0.01% Tween 80, pH 7.8 at room temperature. Plasminogen activation by Mutant 1 in the presence of fibrin fragment E-2 was only about 40% of that of native pro-UK. Native pro-UK plasminogen activation is 250-fold greater in the presence of fibrin fragment $E_2$ than in the absence of fibrin promotion.

Plasmin Sensitivity Assay

The plasmin sensitivity assay is a kinetic study of pro-UK mutant activation by Lys-plasmin. A range of concentrations of pro-UK Mutant 1 (0, 0.1, 0.2, 0.4, 0.6, 0.8, 1.0, 1.2, 1.4, 2.5, 3.5 & 5.0 μM) was incubated with Lys-plasmin (0.1 nM) in the presence of 1.2 mM S2444 in 0.05 M Tris. HCl, 0.15

M NaCl, 0.01 M CaCl$_2$ and 0.01% Tween 80, pH 7.4 at room temperature over time. The same range of concentrations of the pro-UK mutant without plasmin was incubated with S2444 as a control. The 0.1 nM plasmin has no direct effect on S2444 hydrolysis under control condition. The amount of UK generated from pro-UK Mutant 1 was measured by the OD increase with time at 410 nm against a reference wavelength of 490 nm (410/490 nm) on a microtiter plate reader (MR 5000; Dynatech Laboratories, Inc., Alexandria, Va.). It was found that Mutant 1 had a plasmin sensitivity similar to that of native pro-UK, which has a $K_M$ of 2.44 µM, and a $k_{cat}$ of 3.04 nanoM/min.

Plasma Fibrinogenolytic Activity Assay

Pro-UK Mutant 1 (0–100 µg/ml) or pro-UK (0–10 µg/ml) were incubated in 1.0 ml of pooled bank plasma at 37° C. for 6, 16, or 24 hours, after which 0.2 ml of aprotinin (10,000 KIU/ml) was added, and plasma fibrinogen remaining after a given time was measured by the thrombin-clotting method. Mutant 1 had a plasma fibrinogenolytic activity that was about 100-fold lower than that of native pro-UK, i.e., whereas 1.0 µg/ml of native pro-UK will lyse 50% of 9.0 µg/ml fibrinogen within 6 hours, it took 100 µg/ml of Mutant 1 to achieve the same effect.

Fibrin Clot Lysis Assay $^{125}$I-labelled clots prepared from 0.25 ml plasma were prepared as described in Gurewich et al., Clin.Invest., 73:1731 (1980). Clot lysis experiments were performed in 3 ml plasma with a range of concentrations of pro-UK Mutant 1 (10, 20, 30, 40, 70 and 80 µg/ml) or t-PA (5, 10, 30, 50, 75, 100 and 150 ng/ml), and certain combinations of t-PA and pro-UK mutant. Lysis was quantitated from the release of radioactivity and expressed as a percent of the value at complete lysis against time. Mutant 1 fibrin clot lysis activity was 50% of that of native pro-UK, i.e., whereas 200 U/ml native pro-UK will lyse a clot (1 cm$^3$) within 6 hours, it took 12 hours of the same amount of Mutant 1 to achieve the same effect.

Therapeutic Use of Pro-UK Mutants

The pro-UK mutants are used and administered as thrombolytic agents in the same way as pro-UK and UK. The mutant pro-UKs are mixed with a pharmaceutically acceptable carrier, e.g., saline, and administered by, intravascular, e.g., intravenous or intra-arterial, or subcutaneous injection. The pro-UK mutants are injected as a bolus of approximately 20 to 60 mg, or may be infused intravenously at a rate of 40–80 mg/hour. Since the pro-UK mutants have a far greater plasma stability, and are far less likely to induce non-specific plasminogen activation than native pro-UK, higher dosages, e.g., infusions of up to 200 mg/hour may also be used.

Other Embodiments

Other embodiments are within the following claims.

We claim:

1. A thrombolytically active pro-urokinase (pro-UK) mutant consisting of the amino acid sequence of native pro-UK, except wherein said sequence includes one or more substitution mutations of a new histidine or alanine amino acid for a native amino acid at amino acid locations 299, 300, 301, or 313, or of a new glycine amino acid at amino acid location 306 in the amino acid sequence of native pro-UK, and wherein said mutation causes said pro-UK mutant to induce less fibrinogenolysis and non-specific plasminogen activation than native pro-UK when administered to a patient.

2. The pro-UK mutant of claim 1, wherein said mutation causes said pro-UK mutant to have at least a 10-fold lower intrinsic activity than native pro-UK, and to have substantially the same fibrin promotion and thrombolytic activity after plasmin activation compared to native pro-UK when administered to a patient.

3. The pro-UK mutant of claim 1, wherein said new alanine or histidine amino acid is substituted for $Lys^{300}$.

4. The pro-UK mutant of claim 3, wherein said new amino acid is alanine.

5. The pro-UK mutant of claim 3, wherein a new histidine amino acid is substituted for $Gly^{299}$.

6. The pro-UK mutant of claim 3, wherein a new alanine amino acid is substituted for $Glu^{301}$.

7. The pro-UK mutant of claim 1, wherein said new alanine or histidine amino acid is substituted for $Lys^{313}$.

8. The pro-UK mutant of claim 1, wherein said new glycine amino acid is substituted for $Tyr^{306}$.

9. A method of treating thromboembolism in a patient comprising administering a thrombolytic amount of the pro-UK mutant of claim 2 to the patient.

* * * * *